(12) United States Patent
Aubert

(10) Patent No.: US 7,175,699 B2
(45) Date of Patent: Feb. 13, 2007

(54) FILTER ASSEMBLY

(75) Inventor: Bruno Aubert, Connaux (FR)

(73) Assignee: NV Bekaert SA, Zwevegem (BE)

( * ) Notice: Subject to any disclaimer, the term of this patent is extended or adjusted under 35 U.S.C. 154(b) by 84 days.

(21) Appl. No.: 10/380,006

(22) PCT Filed: Sep. 6, 2001

(86) PCT No.: PCT/EP01/10308

§ 371 (c)(1),
(2), (4) Date: Apr. 11, 2003

(87) PCT Pub. No.: WO02/20064

PCT Pub. Date: Mar. 14, 2002

(65) Prior Publication Data

US 2003/0177907 A1 Sep. 25, 2003

(51) Int. Cl.
*B01D 35/06* (2006.01)

(52) U.S. Cl. ............................ 96/224; 55/473; 55/499; 55/521; 55/523; 55/356; 55/DIG. 29; 95/273; 96/223; 96/225

(58) Field of Classification Search ................. 55/356, 55/473, 499, 521, 523, DIG. 29; 95/273, 95/224, 225, 223; 137/528; 96/223–225
See application file for complete search history.

(56) References Cited

U.S. PATENT DOCUMENTS

| | | | | |
|---|---|---|---|---|
| 4,707,167 A | * | 11/1987 | Saito et al. | .................... 96/225 |
| 4,731,100 A | | 3/1988 | Loeffelmann et al. | |
| 5,819,793 A | * | 10/1998 | Rajewski | ..................... 137/528 |
| 6,811,593 B2 | * | 11/2004 | Hansson et al. | ............... 95/273 |
| 2003/0170157 A1 | | 9/2003 | Aubert | |

FOREIGN PATENT DOCUMENTS

| | | |
|---|---|---|
| EP | 0 796 625 A2 | 9/1997 |
| WO | WO 98/00001 A2 | 1/1998 |
| WO | WO 99/03559 A1 | 1/1999 |

* cited by examiner

*Primary Examiner*—Duane Smith
*Assistant Examiner*—Minh-Chau T. Pham
(74) *Attorney, Agent, or Firm*—Foley & Lardner LLP

(57) ABSTRACT

A filter assembly including a filter medium installed in at least one receptacle. The filter assembly includes a heating system to heat the filter medium. The filter medium includes metal fibers. The receptacle or receptacles are provided with at least one air inlet and with at least one air outlet and a device to eliminate the air and free space around and in the filter medium. The receptacles may include at least two deformable walls, which are membranes made of a polymeric or elastomeric material, and the filter medium may include at least one sintered, non-woven metal fiber web.

20 Claims, 1 Drawing Sheet

FILTER ASSEMBLY

FIELD OF THE INVENTION

The invention relates to a filter assembly holding a filter medium provided with means to disinfect the filter medium. The invention further relates to a method to disinfect a filter medium.

BACKGROUND OF THE INVENTION

It is well-known that airborne microorganisms like germs, viruses, fungi and bacteria may cause diseases. Recent studies have indicated that indoor air pollution may pose a great health risk. Indoor air pollution is in most cases caused by the presence of unwanted particulates, unwanted chemical substances and/or unwanted microorganisms.

Unwanted particulates and unwanted chemical substances can in most cases be avoided by conventional techniques such as filtration and ventilation. The contamination by microorganisms creates a more serious obstacle.

HEPA (High Efficiency Particulate Arresting filters) can be used to filter the incoming air by retaining unwanted particulates and unwanted microorganisms such as bacteria.

However, the conditions of the filter medium, such as temperature and humidity, are very favorable to cause a proliferation and dissemination of the germs over the entire thickness and the entire surface of the filter medium. Already after a few hours of operating the filter is contaminated with microorganisms.

A contaminated central air system can become a breeding ground for biological contaminants and the air forced through the air system can distribute the contaminants throughout the building.

In order to avoid a proliferation and dissemination of germs, the filter medium has to be disinfected at regular times. This can for example be achieved by a chemical or thermal treatment.

At present also a photocatalytic process using ultraviolet radiation with titanium dioxide as photocatalyst is known to disinfect a filter medium. However, this technique is only suitable for surface filtration.

SUMMARY OF THE INVENTION

It is an object of the present invention to provide a filter assembly holding a filter medium provided with means to disinfect the filter medium. It is a further object to provide a method of disinfecting a filter medium in an efficient and economical way.

According to a first aspect of the invention a filter assembly is provided. The filter assembly comprises a filter medium, at least one receptacle and a heating system to heat the filter medium. The filter medium comprises metal fibers and is installed in the receptacle.

Possibly, the filter medium is installed in a number of receptacles which are for example placed next to each other. The receptacle or receptacles is/are provided with at least one air inlet, at least one air outlet and with means to eliminate the air and the free space around and in the filter medium In a preferred embodiment of the present invention, a receptacle comprises at least two deformable walls to eliminate the air and free space around and in the filter medium. With deformable is meant that the wall can be deformed in an elastic way, which means that the deformation is reversible. One of the deformable walls can be placed against the upper face of the filter medium while the other can be placed against its lower face. The deformable walls are for example polymeric or elastomeric membranes. It is clear that the deformable walls have to withstand the temperatures applied during the heating of the filter medium.

Deformable walls may be made of silicon or of a fluoroelastomer. Such deformable walls of this type may be made from the fluoroelastomer VITON®.

The filter medium may comprise a sintered, non-woven metal fiber web or a layered structure comprising a number of sintered, non-woven metal fiber webs.

Metal fibers used for the filter medium according to the invention may be made of conventional metals or metal alloys. Exemplary alloys that may be used are stainless steels such as stainless steel 316L, the iron chrome alloy FECRALLOY®, and nickel chrome alloys such as HASTELLOY®, INCONEL®, NICHROME®, and Alloy HR.

The fibers of the filter medium preferably have a diameter ranging between 0.5 and 30 µm. More preferably, the metal fibers have a diameter between 0.5 and 7 µm, for example 1.5 µm.

In one embodiment, the filter medium comprises at least two layers, each layer comprising a non-woven metal fiber web.

The metal fibers of the first layer, at the flow in side of the air have a diameter between 4 and 8 µm, whereas the fibers of the second layer have a diameter between 1 and 3 µm. The second layer is brought into contact with the first layer at the flow out side of this first layer and the thus formed layered filter medium is subsequently sintered and compacted.

In a further embodiment, the filter medium comprises three layers, each layer comprising a non-woven metal fiber web. The fibers of the first layer have a diameter between 8 and 14 µm; the fibers of the second layer have a diameter between 4 and 8 µm whereas the fibers of the third layer have a diameter between 1 and 3 µm.

The filter medium has preferably a filter rating in air of at least 0.3 µm.

The filter rating is determined by the particle size 99.97% of which are captured by the filter medium. Bacteria, viruses and fungi have a size between 0,01 and 20 µm. This means that the major part of the bacteria, viruses, fungi is retained by the filter medium used in the present invention.

The filter medium is furthermore characterised by a high porosity. Preferably, the porosity is higher than 70% and more preferably the porosity is higher than 80%, for example 85%.

The receptacle is further provided with a heating system that allows to heat the filter medium to a temperature higher than 100° C. and preferably lower than 250° C.

More preferably, the temperature is between 134 and 150° C., for example 138° C.

The heating can be realised in any way known to a person skilled in the art and may comprise for example heating by means of one or more electrical resistors, a fluid exchangers, a high frequency heater or by a combination thereof.

The heating can be indirect heating, for example by heating the receptacle that subsequently heats the filter medium. Also a direct heating of the filter medium is possible for example by electrical conduction heating, induction heating or high frequency heating.

The filter assembly according to the present invention is in particular suitable to be used in hospitals, operation blocs, clean labs and production rooms for example production rooms for electronic components.

The filter assembly is also suitable to be used in airconditioning systems for example in airconditioning systems of residential buildings.

According to a second aspect of the present invention a method to disinfect a filter medium comprising metal fibers is provided. The filter medium comprises a sintered, non-woven metal fiber web or a layered structure comprising a number of sintered, non-woven metal fiber webs.

The method comprises the heating of the filter medium under a water vapour and/or radical pressure to disinfect the filter medium. The water vapour pressure and/or radical pressure is obtained during the heating by evaporating the water and the radicals absorbed and/or formed in a natural way at the surface and/or in the porous structure of the filter medium.

The water vapour and/or radical pressure is preferably higher than 1 bar, for example 2 bar or 3.4 bar. The radicals are preferably hydroxyl (OH) radicals. OH radicals are known as very reactive free radicals and as strong oxidants which may kill diverse microorganisms and degrade diverse volatile organic compounds.

Possibly, the radicals comprise also CO radicals.

In a preferred method the water and radical pressure is obtained by eliminating, before the heating, all or substantially all the air and the free space around and in the filter medium in order to allow the water and the radicals absorbed and/or formed in a natural way at the surface and/or in the porous structure of the filter medium to be sufficiently numerous to obtain a saturated or substantially saturated water vapour pressure during the heating of the filter medium.

With a substantially saturated water vapour pressure is meant a pressure that is at least 90% of the saturated water vapour pressure.

With the elimination of substantially all the air and the free space around and in the filter medium is meant the elimination of the air and free space so that a substantially saturated water vapour is obtained.

It is known that all materials in atmospheric conditions absorb a small quantity of water on their surface and that this water presents itself partly under a radical form due to the interaction with the material. Materials made of metal, such as the filter medium comprising metal fibers absorb water and radicals easily.

Since the filter medium is a porous medium, the water and radicals are not only condensed at the outer surface of the filter medium but also in the porous structure of the filter medium itself.

In order to guarantee that the water and the radicals, such as OH radicals are systematically present under the form of vapour, at the surface and/or in the porous structure of the filter medium, preferably substantially all the air and free space around and in the filter medium is eliminated. More preferably, all the air and free space around and in the filter medium is eliminated.

In that way, the water and the radicals that are absorbed or naturally formed at the surface and/or in the porous structure of the filter medium will allow to obtain a saturated or substantially saturated water vapour when the filter medium is heated to temperatures over 100° C.

By the elimination or substantial elimination of the air and free space in and around the filter medium, the water and the OH radicals absorbed or naturally formed at the surface and/or in the porous structure of the filter medium will, when they are completely or partly evaporated through the heating process at temperatures over 100° C., finally be highly concentrated in the very small remaining volume and the vapour or radicals and germs will very probably meet.

The action of such a radical-charged water vapour is extremely efficient to destroy germs.

A preferred method comprises the following steps:
providing a filter assembly as described above;
eliminating all or substantially all the air and free space around and in the filter medium;
establishing airtight conditions;
creating a saturated or substantially saturated water vapour and/or radical pressure by heating the filter medium.

The air and free space around and in the filter medium is eliminated by reducing the volume of one or more receptacles holding the filter medium. This can be realised by placing the deformable walls of the receptacle against the upper and lower face of the filter medium.

In a subsequent step airtight conditions are established for example by closing the receptacle in an airtight way.

It is preferred that a light vacuum is created subsequently by slightly decreasing the pressure by suction or by slightly increasing the volume of the residual free space around and in the filter medium before the heating.

The presence of a light vacuum is helping to reach a saturated or substantially saturated vapour pressure during the subsequent heating more easily.

Subsequently, the filter medium is heated to a temperature higher than 100° C. Preferably, the temperature is between 100 and 250° C. and more preferably between 134 and 150° C., for example 138° C.

The heating can be realised by any method known in the art.

The time period of the heat treatment is preferably between 1 and 60 minutes. It is clear that the time period of the heat treatment is dependent upon the temperature. In a preferred method the heat treatment comprises heating at a temperature of 138° C. during 20 minutes.

BRIEF DESCRIPTION OF THE DRAWINGS

The invention will now be described into more detail with reference to the accompanying drawings wherein.

DESCRIPTION OF THE PREFERRED EMBODIMENTS OF THE INVENTION

Figure 1:
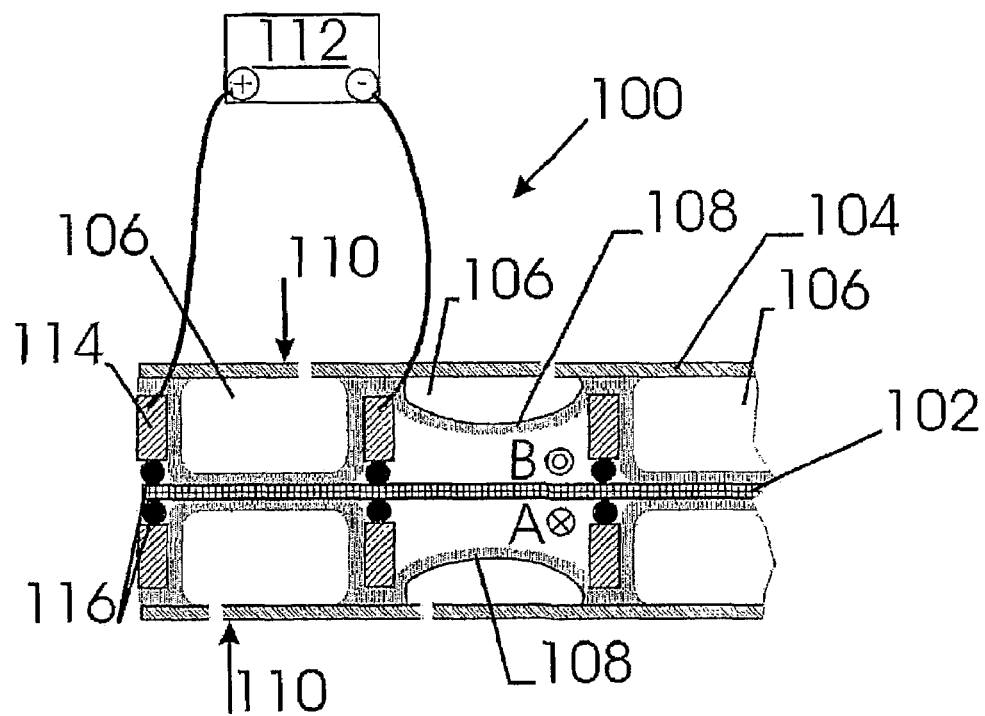
FIG. 1 and FIG. 2 show two embodiments of a filter assembly according to the present invention.

Referring to FIG. 1, the filter assembly 100 comprises a filter medium 102 and a filter box 104.

The filter medium comprises a sintered, non-woven metal fiber web. The metal fibers are stainless steel fibers having a diameter of 1.5 µm. The filter rating of the filter medium in air is 0.3 µm.

The filter box is divided in a number of compartments or receptacles 106, placed next two each other.

Each of the compartments can be sealed in an airtight manner for example by means of spacing rings 114 and gaskets 116. This allows it to keep one or more compartments impermeable for the air flow to be filtered while the other compartments are still functioning as filter units.

Each receptacle 106 comprises at least one air inlet, at least one air outlet and two membranes 108 made of a fluoroelastomer VITON®). During a normal filtration regime, the membranes are loose and the air to be filtered passes from face A to face B.

During a normal filtration regime, the membranes are loose and the air to be filtered passes from face A to face B.

Periodically, for example every 6 hours, the volume of a deformable receptacle is reduced while the other compartments are still functioning as filtration units.

The volume of a receptacle can be reduced by stretching the membranes 108 on the upper and lower face of the filter medium 102. This can be realised by introducing compressed air through the opening 110. The pressure phase caused by the arrival of compressed air is possibly followed by a depressure phase to create a light vacuum. The presence of a light vacuum allows to obtain the saturated vapour pressure in a better way.

Once a light vacuum is obtained, the filter medium is heated to a temperature of 138° C. during 20 minutes. The filter medium is for example heated by applying an electrical current, controlled by a generator 112, between the two spacing rings 114 to heat up the relevant part of the filter medium. Reckoning with the quasi absence of free air around and in the filter medium, the water and the OH radicals absorbed or naturally formed in the filter, will allow an optimal sterilisation.

After the heat treatment, the germs are killed and the filter medium is disinfected. Germs may no longer proliferate or migrate.

This operation can be repeated consecutively for all receptacles.

Figure 2:
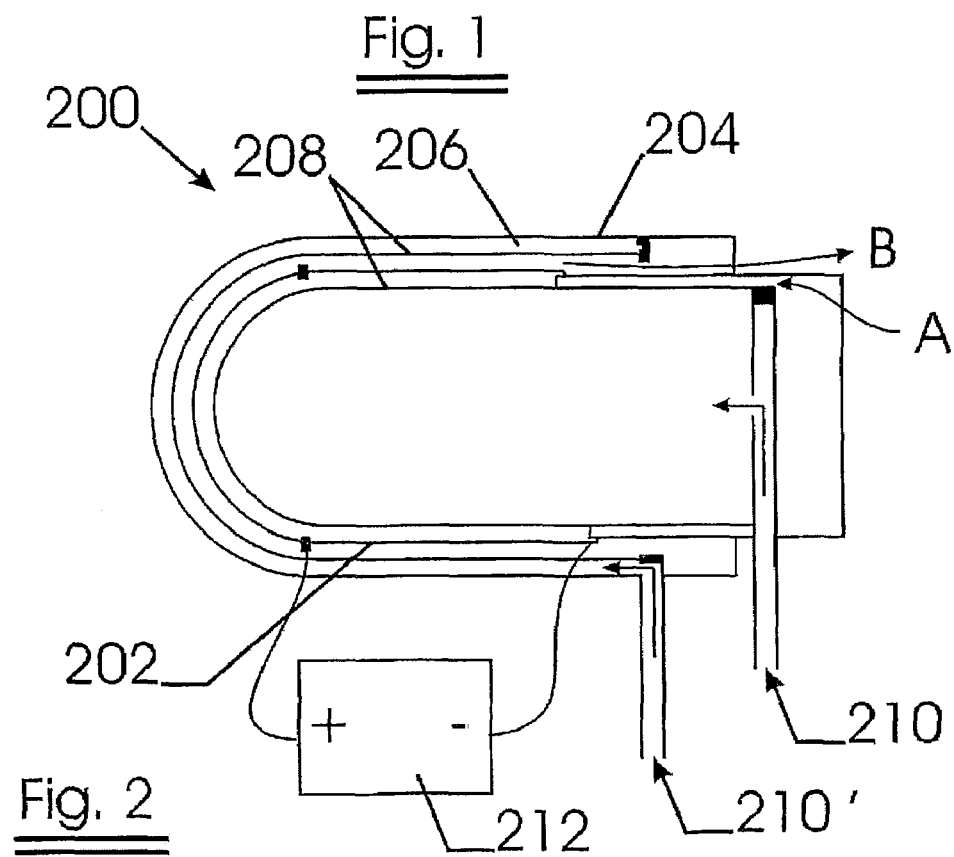

FIG. 2 shows an alternative embodiment of a filter assembly 200 according to the present invention.

A filter compartment 206 comprises a tubular filter medium 202 and two membranes 208.

The volume of the air around and in the filter medium can be reduced by stretching the membranes 208 on the two faces of the filter medium, for example by introducing compressed air through the openings 210 and 210'.

The filter medium is heated by applying an electrical current controlled by a generator 212.

The invention claimed is:

1. A filter assembly comprising a filter medium, at least one receptacle and a heating system to heat the filter medium; said filter medium comprising metal fibers and being installed in said receptacle or receptacles; said receptacle or receptacles being provided with at least one air inlet, with at least one air outlet and with means to eliminate the air and free space around and in the filter medium, wherein the filter assembly is adapted to obtain at least one of (i) a saturated water vapour and/or radical pressure and (ii) at least 90% of a saturated water vapour and/or radical pressure, and wherein the filter assembly is adapted to heat the filter medium to substantially sterilize the filter medium under the at least one of the saturated water vapour and/or radical pressure and the at least 90% of the saturated water vapour and/or radical pressure.

2. A filter assembly according to claim 1, wherein said receptacle comprises at least two deformable walls.

3. A filter assembly according to claim 2, wherein said deformable walls are membranes made of a polymeric or elastomeric material.

4. A filter assembly according to claim 1, wherein said filter medium comprises at least one sintered, non-woven metal fiber web.

5. A filter assembly according to claim 1, wherein said metal fibers are stainless steel fibers having a diameter between 1 and 22 µm.

6. A filter assembly according to claim 1, wherein said filter medium has a filter rating in air of at least 0.3 µm.

7. A method to disinfect a filter medium comprising metal fibers by heating the filter medium under a water vapour and/or radical pressure to disinfect the filter medium, wherein said water vapour and/or radical pressure is a saturated or substantially saturated water vapour pressure.

8. A method according to claim 7, wherein said water vapour and/or radical pressure is obtained by eliminating all or substantially all the air and free space around and in said filter medium before said heating.

9. A method according to claim 7, wherein said filter medium comprises at least one sintered, non-woven metal fiber web.

10. A method according to claim 7, said method comprising the steps of:
providing a filter assembly comprising the filter medium, at least one receptacle and a heating system to heat the filter medium; said filter medium comprising metal fibers and being installed in said receptacle or receptacles; said receptacle or receptacles being provided with at least one air inlet, with at least one air outlet and with means to eliminate the air and free space around and in the filter medium;
eliminating all or substantially all the air and free space around and in the filter medium;
establishing airtight conditions; and
creating the saturated or substantially saturated water vapour and/or radical pressure by heating the filter medium.

11. A method according to claim 10, said method comprising the step of creating a light vacuum by suction or by slightly increasing the volume of the residual free space around and in the filter medium after the airtight conditions are established.

12. A method according to claim 7, wherein said filter medium is heated to a temperature of at least 100°C.

13. A filter assembly comprising:
a filter medium installed in one or more receptacles, wherein one or more of the receptacles are adapted to expand from a retracted state where first and second major surfaces of the filter medium opposite to one another are not substantially against one or more of the receptacles, to a state where the first and second major surfaces of the filter medium opposite to one another are substantially against one or more of the receptacles; and
a heating system;
wherein the filter assembly is adapted to obtain at least one of a water vapour pressure and a radical pressure about the filter medium, wherein the water vapor pressure is at least one of a saturated water vapour pressure and a substantially saturated water vapour pressure; and
wherein the heating system is adapted to heat the filter medium to substantially sterilize the filter medium under the at least one of the water vapour pressure and the radical pressure.

14. The assembly of claim 13, wherein the filter assembly is further adapted to effectively reduce air and free space around and in the filter medium such that at least one of the water vapour pressure and the radical pressure is obtained.

15. The assembly of claim 13, wherein the receptacle comprises at least two deformable walls.

16. The assembly of claim 15, wherein the deformable walls are membranes made of a polymeric or elastomeric material.

17. The assembly of claim 13, wherein the filter medium comprises at least one sintered, non-woven metal fiber web.

18. The assembly of claim 13, wherein the filter assembly is adapted to obtain at least one of the water vapour pressure and the radical pressure about the filter medium when the receptacle is in the expanded state.

19. The assembly of claim 13, wherein the filter assembly is adapted to substantially expel air about and in the filter medium when the receptacle is in the expanded state, and wherein the filter assembly is adapted to obtain a light vacuum about and in the filter medium after the receptacle has been expanded to the expanded state to obtain at least one of a water vapour pressure and a radical pressure about the filter medium.

20. A filter assembly comprising a filter medium, at least one receptacle and a heating system to heat the filter medium; said filter medium comprising metal fibers and being installed in said receptacle or receptacles; said receptacle or receptacles being provided with at least one air inlet, with at least one air outlet and with a device adapted to eliminate the air and free space around and in the filter medium, wherein the filter assembly is adapted to obtain at least one of (i) a saturated water vapour and/or radical pressure and (ii) at least 90% of a saturated water vapour and or radical pressure, and wherein the filter assembly is adapted to heat the filter medium to substantially sterilize the filter medium under the at least one of the saturated water vapour and/or radical pressure and the at least 90% of the saturated water vapour and/or radical pressure.

* * * * *